(12) United States Patent
Henkel (10) Patent No.: US 10,087,221 B2
(45) Date of Patent: Oct. 2, 2018

(54) SYNTHESIS OF HYDANTOIN CONTAINING PEPTIDE PRODUCTS

(71) Applicant: SANOFI-AVENTIS DEUTSCHLAND GMBH, Frankfurt am Main (DE)

(72) Inventor: Bernd Henkel, Frankfurt am Main (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 14/778,496

(22) PCT Filed: Mar. 19, 2014

(86) PCT No.: PCT/EP2014/055506
§ 371 (c)(1),
(2) Date: Sep. 18, 2015

(87) PCT Pub. No.: WO2014/147124
PCT Pub. Date: Sep. 25, 2014

(65) Prior Publication Data
US 2016/0289282 A1 Oct. 6, 2016

(30) Foreign Application Priority Data

Mar. 21, 2013 (EP) .................... 13160384

(51) Int. Cl.
*C07K 14/47* (2006.01)
*C07K 1/04* (2006.01)
*C07K 1/107* (2006.01)
*C07D 233/78* (2006.01)

(52) U.S. Cl.
CPC ............ *C07K 14/47* (2013.01); *C07D 233/78* (2013.01); *C07K 1/04* (2013.01); *C07K 1/107* (2013.01)

(58) Field of Classification Search
CPC .......... C07K 1/04; C07K 1/107; C07K 14/47; C07D 233/78
See application file for complete search history.

(56) References Cited

U.S. PATENT DOCUMENTS

| | | | |
|---|---|---|---|
| 3,835,175 A | 9/1974 | Carpino et al. |
| 3,906,031 A | 9/1975 | Carpino et al. |
| 4,108,846 A | 8/1978 | Carpino et al. |
| 4,755,591 A | 7/1988 | Koenig et al. |
| 5,169,932 A | 12/1992 | Hoeger et al. |
| 5,175,254 A | 12/1992 | Bernard et al. |
| 5,247,067 A | 9/1993 | Terukatsu et al. |
| 5,296,468 A | 3/1994 | Hoeger et al. |
| 5,352,796 A | 10/1994 | Hoeger et al. |
| 5,460,786 A | 10/1995 | Nokihara |
| 5,478,810 A | 12/1995 | Stueber et al. |
| 5,502,165 A | 3/1996 | Ho et al. |
| 5,503,805 A | 4/1996 | Sugarman et al. |
| 5,516,891 A | 5/1996 | Siwruk et al. |
| 5,536,816 A | 7/1996 | Hohler et al. |
| 5,563,032 A | 10/1996 | Fields et al. |
| 5,565,574 A | 10/1996 | Hoeger et al. |
| 5,576,296 A | 11/1996 | Bartfai et al. |
| 5,580,957 A | 12/1996 | Hoeger et al. |
| 5,602,230 A | 2/1997 | Heavner et al. |
| 5,602,231 A | 2/1997 | Cotton et al. |
| 5,607,858 A | 3/1997 | Stueber et al. |
| 5,614,608 A | 3/1997 | Krchnak et al. |
| 5,618,785 A | 4/1997 | Heavner et al. |
| 5,639,603 A | 6/1997 | Sugarman et al. |
| 5,665,975 A | 9/1997 | Sugarman et al. |
| 5,708,153 A | 1/1998 | Dower et al. |
| 5,710,123 A | 1/1998 | Heavner et al. |
| 5,710,249 A | 1/1998 | Hoeger et al. |
| 5,736,315 A | 4/1998 | Fields et al. |
| 5,744,450 A | 4/1998 | Hoeger et al. |
| 5,750,649 A | 5/1998 | Hohler et al. |
| 5,770,358 A | 6/1998 | Dower et al. |
| 5,773,575 A | 6/1998 | Ho et al. |
| 5,789,162 A | 8/1998 | Dower et al. |
| 5,830,637 A | 11/1998 | Frank et al. |
| 5,891,640 A | 4/1999 | Frank et al. |
| 5,916,876 A | 6/1999 | Heavner et al. |
| 6,022,685 A | 2/2000 | Fields et al. |
| 6,028,168 A | 2/2000 | Goodman et al. |
| 6,040,423 A | 3/2000 | Frank et al. |
| 6,056,926 A | 5/2000 | Sugarman et al. |
| 6,111,065 A | 8/2000 | Heavner et al. |
| 6,136,781 A | 10/2000 | Kitada et al. |
| 6,140,493 A | 10/2000 | Dower et al. |
| 6,143,497 A | 11/2000 | Dower et al. |
| 6,165,717 A | 12/2000 | Dower et al. |
| 6,165,730 A | 12/2000 | De Leys |
| 6,165,778 A | 12/2000 | Kedar et al. |

(Continued)

FOREIGN PATENT DOCUMENTS

| | | |
|---|---|---|
| CA | 2104099 | 8/1993 |
| CA | 2050216 | 3/2003 |

(Continued)

OTHER PUBLICATIONS

Bray, Nature Reviews, Drug Discovery (2003) vol. 2, 587-593.*

(Continued)

*Primary Examiner* — Julie Ha
*Assistant Examiner* — Li N Komatsu
(74) *Attorney, Agent, or Firm* — McDonnell Boehnen Hulbert & Berghoff LLP (57) ABSTRACT

The present invention relates to a method of synthesizing a peptide product comprising at least one hydantoin group. The peptide product may be used as a reference material for the quality control of pharmaceutical peptides, particularly for the quality control of exendin peptides. Further, the invention relates to hydantoin building blocks, a method for manufacturing such building blocks and their use for the synthesis of peptide products.

10 Claims, 3 Drawing Sheets
Specification includes a Sequence Listing.

(56) References Cited

U.S. PATENT DOCUMENTS

| | | |
|---|---|---|
| 6,210,903 B1 | 4/2001 | De Leys |
| 6,268,339 B1 | 7/2001 | De Leys |
| 6,416,949 B1 | 7/2002 | Dower et al. |
| 6,469,136 B1 | 10/2002 | Bray et al. |
| 6,476,186 B1 | 11/2002 | Hsieh et al. |
| 6,492,460 B2 | 12/2002 | Haq et al. |
| 6,617,307 B1 | 9/2003 | Nishimura et al. |
| 6,649,735 B1 | 11/2003 | De Leys |
| 6,667,387 B1 | 12/2003 | De Leys |
| 6,673,769 B2 | 1/2004 | Goodman et al. |
| 6,703,480 B1 | 3/2004 | Balu |
| 6,709,828 B1 | 3/2004 | De Leys |
| 6,747,125 B1 | 6/2004 | Hoeger et al. |
| 6,767,993 B2 | 7/2004 | Bray et al. |
| 6,809,190 B2 | 10/2004 | Ikeda et al. |
| 6,849,710 B1 | 2/2005 | Arzeno |
| 7,009,037 B2 | 3/2006 | Sorensen |
| 7,049,293 B2 | 5/2006 | Nishimura et al. |
| 7,138,489 B2 | 11/2006 | Nishimura et al. |
| 7,176,282 B1 | 2/2007 | Holm et al. |
| 7,183,430 B2 | 2/2007 | Montiel et al. |
| 7,235,242 B2 | 6/2007 | Achtman et al. |
| 7,329,646 B2 | 2/2008 | Sun et al. |
| 7,348,404 B2 | 3/2008 | Holm et al. |
| 7,393,920 B2 | 7/2008 | Collins et al. |
| 7,402,663 B2 | 7/2008 | Collins et al. |
| 7,414,106 B2 | 8/2008 | Camarero et al. |
| 7,414,107 B2 | 8/2008 | Larsen et al. |
| 7,417,028 B2 | 8/2008 | Ewing et al. |
| 7,425,541 B2 | 9/2008 | Dubois et al. |
| 7,439,222 B2 | 10/2008 | Guinn et al. |
| 7,459,522 B2 | 12/2008 | Balu |
| 7,507,791 B2 | 3/2009 | Skripko |
| 7,534,763 B2 | 5/2009 | Qian et al. |
| 7,550,560 B2 | 6/2009 | Collins et al. |
| 7,563,865 B2 | 7/2009 | Collins et al. |
| 7,582,728 B2 | 9/2009 | Collins et al. |
| 7,598,222 B2 | 10/2009 | Prouty et al. |
| 7,612,168 B2 | 11/2009 | Sorensen |
| 7,691,968 B2 | 4/2010 | Evans et al. |
| 7,745,570 B2 | 6/2010 | Tomich et al. |
| 7,834,142 B2 | 11/2010 | Li |
| 7,902,488 B2 | 3/2011 | Collins et al. |
| 7,935,786 B2 | 5/2011 | Larsen |
| 7,939,628 B2 | 5/2011 | Collins et al. |
| 7,960,349 B2 | 6/2011 | Ewing et al. |
| 7,960,506 B2 | 6/2011 | Nash |
| 7,981,998 B2 | 7/2011 | Nash |
| 8,034,787 B2 | 10/2011 | Dubois |
| 8,058,393 B2 | 11/2011 | Collins et al. |
| 8,058,394 B2 | 11/2011 | Kajihara et al. |
| 8,097,586 B2 | 1/2012 | Lv et al. |
| 8,114,959 B2 | 2/2012 | Juul-Mortensen |
| 8,153,761 B2 | 4/2012 | Collins et al. |
| 8,178,474 B1 | 5/2012 | Melnyk et al. |
| 8,202,837 B2 | 6/2012 | Bush et al. |
| 8,227,571 B2 | 7/2012 | Chen et al. |
| 8,252,896 B2 | 8/2012 | Hsiao et al. |
| 8,426,560 B2 | 4/2013 | Collins et al. |
| 8,435,800 B2 | 5/2013 | Gengrinovitch |
| 8,609,809 B2 | 12/2013 | Nash |
| 8,620,595 B2 | 12/2013 | Krokhin et al. |
| 8,710,011 B2 | 4/2014 | Garcia et al. |
| 8,716,221 B2 | 5/2014 | Lv et al. |
| 8,802,819 B2 | 8/2014 | Fernando et al. |
| 8,846,862 B2 | 9/2014 | Collins et al. |
| 8,933,196 B2 | 1/2015 | Chen et al. |
| 8,946,166 B2 | 2/2015 | Garcia et al. |
| 8,993,716 B2 | 3/2015 | Carreno et al. |
| 9,175,056 B2 | 11/2015 | Nash |
| 9,206,223 B2 | 12/2015 | Nash et al. |
| 9,211,522 B2 | 12/2015 | Collins et al. |
| 9,260,474 B2 | 2/2016 | Pan et al. |
| 9,263,194 B2 | 2/2016 | Seo et al. |
| 9,266,921 B2 | 2/2016 | Garcia et al. |
| 9,290,537 B2 | 3/2016 | Madded et al. |
| 9,314,521 B2 | 4/2016 | Ossendorp et al. |
| 9,315,564 B2 | 4/2016 | Serraima et al. |
| 9,364,772 B2 | 6/2016 | Larsen et al. |
| 9,393,186 B2 | 7/2016 | Alminana et al. |
| 9,394,336 B2 | 7/2016 | Nash et al. |
| 9,394,341 B2 | 7/2016 | Wen et al. |
| 9,422,330 B2 | 8/2016 | Wu et al. |
| 9,605,344 B2 | 3/2017 | Jiang et al. |
| 9,724,622 B2 | 8/2017 | Anwer |
| 9,766,217 B2 | 9/2017 | Kidal et al. |
| 2002/0058788 A1 | 5/2002 | Sheppeck |
| 2003/0191049 A1 | 10/2003 | Amblard |
| 2004/0235049 A1 | 11/2004 | Melnyk et al. |
| 2006/0079667 A1 | 4/2006 | Skripko |
| 2006/0167224 A1 | 7/2006 | Tonosaki et al. |
| 2007/0129537 A1 | 6/2007 | Camarero et al. |
| 2010/0021510 A1 | 1/2010 | Carreno et al. |
| 2010/0056755 A1 | 3/2010 | Hsiao et al. |
| 2010/0292436 A1 | 11/2010 | Bai et al. |
| 2011/0245461 A1 | 10/2011 | Krokhin et al. |
| 2011/0313131 A1 | 12/2011 | Christelle et al. |
| 2011/0319594 A1 | 12/2011 | Bai et al. |
| 2012/0296068 A1 | 11/2012 | Chen et al. |
| 2013/0289241 A1 | 10/2013 | Bai et al. |
| 2014/0187745 A1 | 7/2014 | Wen et al. |
| 2015/0051372 A1 | 2/2015 | Qin et al. |
| 2015/0073122 A1 | 3/2015 | Seo et al. |
| 2015/0232527 A1 | 8/2015 | Gong et al. |
| 2015/0274799 A1 | 10/2015 | Gong et al. |

FOREIGN PATENT DOCUMENTS

| | | |
|---|---|---|
| CA | 2765196 | 12/2004 |
| CA | 2458084 | 9/2005 |
| CA | 2915484 | 6/2016 |
| CN | 1699404 | 11/2005 |
| CN | 101255191 | 9/2008 |
| CN | 101357937 | 2/2009 |
| CN | 101357938 | 2/2009 |
| CN | 101463078 | 6/2009 |
| CN | 101463081 | 6/2009 |
| CN | 101525368 | 9/2009 |
| CN | 101525370 | 9/2009 |
| CN | 101538324 | 9/2009 |
| CN | 102174082 | 9/2011 |
| CN | 102558338 | 7/2012 |
| CN | 102875663 | 1/2013 |
| CN | 103242443 | 8/2013 |
| CN | 103333237 | 10/2013 |
| CN | 103536912 | 1/2014 |
| CN | 103613655 | 3/2014 |
| CN | 103965285 | 8/2014 |
| CN | 104086631 | 10/2014 |
| CN | 104211801 | 12/2014 |
| CN | 105111303 | 12/2015 |
| CN | 105585612 | 5/2016 |
| DE | 4244565 | 7/1994 |
| DE | 4341471 | 6/1995 |
| DE | 19543628 | 5/1997 |
| EP | 0402313 | 12/1990 |
| EP | 0445801 | 9/1991 |
| EP | 0450715 | 10/1991 |
| EP | 1445260 | 8/2004 |
| EP | 1923397 | 5/2008 |
| FI | 20065208 | 3/2006 |
| FR | 2864830 | 7/2005 |
| GB | 200105069 | 4/2001 |
| GB | 200210185 | 6/2002 |
| GB | 200613147 | 8/2006 |
| NL | 2007536 | 4/2013 |
| WO | WO 91/06543 | 5/1991 |
| WO | WO 92/17025 | 10/1992 |
| WO | WO 92/20709 | 11/1992 |
| WO | WO 93/03056 | 2/1993 |
| WO | WO 93/06121 | 4/1993 |
| WO | WO 93/18054 | 9/1993 |
| WO | WO 93/24526 | 12/1993 |
| WO | WO 93/25571 | 12/1993 |

(56) References Cited

FOREIGN PATENT DOCUMENTS

| WO | WO 94/04568 | 3/1994 |
|---|---|---|
| WO | WO 94/05314 | 3/1994 |
| WO | WO 94/09032 | 4/1994 |
| WO | WO 94/14836 | 7/1994 |
| WO | WO 95/00474 | 1/1995 |
| WO | WO 95/08561 | 3/1995 |
| WO | WO 95/12608 | 5/1995 |
| WO | WO 95/14787 | 6/1995 |
| WO | WO 95/21858 | 8/1995 |
| WO | WO 95/27727 | 10/1995 |
| WO | WO 96/22157 | 7/1996 |
| WO | WO 96/34012 | 10/1996 |
| WO | WO 96/40759 | 12/1996 |
| WO | WO 97/11372 | 3/1997 |
| WO | WO 98/11125 | 3/1998 |
| WO | WO 98/11126 | 3/1998 |
| WO | WO 98/31791 | 7/1998 |
| WO | WO 99/46283 | 9/1999 |
| WO | WO 00/33888 | 6/2000 |
| WO | WO 01/34635 | 5/2001 |
| WO | WO 01/38342 | 5/2001 |
| WO | WO 01/55213 | 8/2001 |
| WO | WO 01/95945 | 12/2001 |
| WO | WO 02/20554 | 3/2002 |
| WO | WO 02/40512 | 5/2002 |
| WO | WO 02/053606 | 7/2002 |
| WO | WO 02/070546 | 9/2002 |
| WO | WO 02/074782 | 9/2002 |
| WO | WO 02/083606 | 10/2002 |
| WO | WO 03/018605 | 3/2003 |
| WO | WO 03/093301 | 11/2003 |
| WO | WO 03/093302 | 11/2003 |
| WO | WO 03/095475 | 11/2003 |
| WO | WO 2004/018502 | 3/2004 |
| WO | WO 2004/022578 | 3/2004 |
| WO | 2004/035623 A2 | 4/2004 |
| WO | WO 2004/089504 | 10/2004 |
| WO | WO 2004/105685 | 12/2004 |
| WO | WO 2004/105790 | 12/2004 |
| WO | WO 2005/019262 | 3/2005 |
| WO | WO 2005/063791 | 7/2005 |
| WO | WO 2005/080424 | 9/2005 |
| WO | WO 2005/087794 | 9/2005 |
| WO | WO 2006/008050 | 1/2006 |
| WO | WO 2006/014287 | 2/2006 |
| WO | WO 2006/040037 | 4/2006 |
| WO | WO 2006/054310 | 5/2006 |
| WO | WO 2006/108594 | 10/2006 |
| WO | WO 2006/117227 | 11/2006 |
| WO | WO 2006/127048 | 11/2006 |
| WO | WO 2006/127948 | 11/2006 |
| WO | WO 2007/033383 | 3/2007 |
| WO | WO 2007/056681 | 5/2007 |
| WO | 2007/068474 A1 | 6/2007 |
| WO | WO 2007/065691 | 6/2007 |
| WO | WO 2007/113356 | 10/2007 |
| WO | WO 2007/113386 | 10/2007 |
| WO | WO 2007/139589 | 12/2007 |
| WO | WO 2007/140284 | 12/2007 |
| WO | WO 2008/001109 | 1/2008 |
| WO | WO 2008/028974 | 3/2008 |
| WO | WO 2008/044890 | 4/2008 |
| WO | 2008/071972 A1 | 6/2008 |
| WO | WO 2008/076904 | 6/2008 |
| WO | 2008/101017 A2 | 8/2008 |
| WO | WO 2008/109079 | 9/2008 |
| WO | WO 2008/137165 | 11/2008 |
| WO | 2008/152403 A1 | 12/2008 |
| WO | WO 2009/003666 | 1/2009 |
| WO | WO 2009/074483 | 6/2009 |
| WO | WO 2009/098707 | 8/2009 |
| WO | WO 2009/106343 | 9/2009 |
| WO | WO 2009/132231 | 10/2009 |
| WO | WO 2009/138488 | 11/2009 |
| WO | 2009/155258 A2 | 12/2009 |
| WO | 2010/011439 A2 | 1/2010 |
| WO | WO 2010/009872 | 1/2010 |
| WO | WO 2010/028122 | 3/2010 |
| WO | WO 2010/028131 | 3/2010 |
| WO | WO 2010/033254 | 3/2010 |
| WO | WO 2010/034032 | 3/2010 |
| WO | WO 2011/107447 | 3/2010 |
| WO | 2010/070251 A1 | 6/2010 |
| WO | 2010/070252 A1 | 6/2010 |
| WO | 2010/070253 A1 | 6/2010 |
| WO | 2010/070255 A1 | 6/2010 |
| WO | WO 2010/063122 | 6/2010 |
| WO | WO 2010/063123 | 6/2010 |
| WO | WO 2010/063124 | 6/2010 |
| WO | 2010/096052 A1 | 8/2010 |
| WO | 2010/096142 A1 | 8/2010 |
| WO | WO 2010/091893 | 8/2010 |
| WO | WO 2010/118880 | 10/2010 |
| WO | 2010/148089 A1 | 12/2010 |
| WO | 2011/006497 A1 | 1/2011 |
| WO | WO 2011/009626 | 1/2011 |
| WO | 2011/011965 A1 | 3/2011 |
| WO | WO 2011/047868 | 4/2011 |
| WO | 2011/075393 A2 | 6/2011 |
| WO | 2011/094337 A1 | 8/2011 |
| WO | 2011/117416 A1 | 9/2011 |
| WO | 2011/119657 A1 | 9/2011 |
| WO | 2011/117415 A1 | 12/2011 |
| WO | 2011/160630 A2 | 12/2011 |
| WO | WO 2011/161007 | 12/2011 |
| WO | WO 2012/055509 | 5/2012 |
| WO | WO 2012/057624 | 5/2012 |
| WO | 2012/088116 A2 | 6/2012 |
| WO | WO 2012/085279 | 6/2012 |
| WO | 2012/138941 A1 | 10/2012 |
| WO | WO 2012/130775 | 10/2012 |
| WO | WO 2012/155780 | 11/2012 |
| WO | WO 2012/161654 | 11/2012 |
| WO | WO 2013/051936 | 4/2013 |
| WO | WO 2013/093639 | 6/2013 |
| WO | WO 2013/156493 | 10/2013 |
| WO | WO 2013/170963 | 11/2013 |
| WO | WO 2014/118797 | 8/2014 |
| WO | WO 2015/009701 | 1/2015 |
| WO | WO 2015/038919 | 3/2015 |
| WO | WO 2015/078477 | 6/2015 |
| WO | WO 2015/128687 | 9/2015 |
| WO | WO 2016/020349 | 2/2016 |
| WO | WO 2016/057683 | 4/2016 |
| WO | WO 2016/067271 | 5/2016 |
| WO | WO 2016/084100 | 6/2016 |
| WO | WO 2017/162653 | 9/2017 |

OTHER PUBLICATIONS

Chong et al., Tetrahedron Letters (1999) 40, 2493-2496.*
Meusel, Organic Preparations and Procedures Int. (2004) 36(5), 391-443.*
Bray, Nature Reviews, Drug Discovery (2003) 2, 537-593.*
Lyxumia Assessment Report, European Medicines Agency, Science Medicines Health, (Nov. 2012) 1-81.*
Barnett, Core Evidence (2011) 6, 67-79.*
Anonymous: Lixisenatide—Wikipedia, the free encyclopedia, Feb. 24, 2013, pp. 1-4, XP055120784, Retrieved from Internet: URL: http://en.wikipedia.org/w/index. php?title= Lixisenatide&olidid= 540119995 (retrieved on May 28, 2014).
Alberico et al. "Mild, orthogonal solid-phase peptide synthesis: use of N alpha-dithiasuccinoyl (Dts) amino acids and N-(iso-propyldithio)carbonylproline, together with p-alkoxybenzyl ester anchoring linkages," Int J Pept Protein Res. 30(2):177-205 (Aug. 1987).
Bhalay et al., "Multiple solid-phase synthesis of hydantoins and thiohydantoins", Mol Divers. 3(3):195-8 (1998).
Chong et al., "Solid phase hydantoin synthesis: An efficient and direct conversion of Fmoc-protected dipeptides to hydantoins", Tetrahedron Letters, 40(13): 2493-2496 (1999).

(56) References Cited

OTHER PUBLICATIONS

Day et al., "A new glucagon and GLP-1 co-agonist eliminates obesity in rodents", Nature Chemical Biology, 5(10): 749-57 (2009).
Hjorth et al., "Glucagon and glucagon-like peptide 1: Selective receptor recognition via distinct peptides epitopes", The Journal of Biological Chemistry, 269(48): 30121-30124 (1994).
Lamothe et al., "Solid-phase preparation of hydantoins through a new cyclizationicleavage step", J. Comb. Chem., 4: 73-78 (2002).
Meusel et al., "Recent developments in hydantoin chemistry. A review", Organic Preparations and Procedures International, Organic Preparation and Procedures Co., Newton Highlands, MA, US, 36(5): 391-443 (2004).
Mhidia et al., "Selective cleavage of an azaGly peptide bond by copper (II). Long-range effect of histidine residue", Journal of Peptide Science, 15: 141-147 (2010).
Nefzi et al., "Combinatorial chemistry: from peptides and peptidomimetics to small organic and heterocyclic compounds", Bioorganic and Medicinal Chemistry Letters, 8: 2273-2278 (1998).
Opacic et al., "Synthesis and X-ray crystal structure study of the hydroxyurea and hydantonin derivatives of L-valine", J. Peptide Res., 66: 85-93 (2005).
Park et al., "Hydantoin formation by cyclo-elimination: reactivity difference between Merrifield- and Wang-derived resins," Tetrahedron Letters, 41: 7409-7413 (2000).
Quibell et al., "Synthesis of azapeptides by the Fmoc-/tert-butyl/polyamide technique", Journal of the Chemical Society, Perkin Transactions 1, 22: 2843-2849 (1993).
Royo et al., "Solid-phase synthesis of constrained RGD scaffolds and their binding to the αvβ3 integrin receptor", Tetrahedron Letters, NL, 42(42): 7387-7391 (2001).
Takeuchi et al., "Synthesis of carbonyl-bridged peptides containing an α-fluoroglycine residue", Chem. Commun., 789-786 (2000).
Vazquez et al., "Re-evaluation of a solid-phase hydantoin synthesis", Letters in Organic Chemistry, 1: 224-226 (2004).
Vazquez et al., "Conformationally restricted hydantoin-based peptidomimetics as inhibitor of Caspase-3 with basic groups allowed at the S3 enzyme subsite", Chem Med Chem, 3: 979-985 (2008).
Witkowska et al., "New analogues of laminin active fragment YIGSR: synthesis and biological activityin vitro andin vivo", Journal of Peptide Science, 10(5): 285-290 (2004).
Xiao et al., "Selective solid phase synthesis of ureas and hydantoins from common phenyl cabamate intermediates", Journal of Organic Chemistry, 62: 6968-6973 (1997).
Yahalom et al., "Structure-activity studies of reduced-size gonadotropin-releasing hormone agonists derived from the sequence of an endothelin antagonist", Journal of Medicinal Chemistry, 43(15): 2824-2830 (2000).
Zhang et al., "Synthesis of hydantoins from entantiomerically pure alpha-amino amides without epimerization", J. Org. Chem., 71: 1750-1753 (2006).
Extended European Search Report issued in European Application No. 13160384.7 (dated Jul. 9, 2013).
International Search Report and Written Opinion issued in International Patent Application No. PCT/EP2014/055506 (dated Jun. 17, 2014).
International Preliminary Report on Patentability (Chapter II) issued in International Patent Application No. PCT/EP2014/055506 (dated Apr. 17, 2015).

* cited by examiner

SYNTHESIS OF HYDANTOIN CONTAINING PEPTIDE PRODUCTS

This application is a national stage application under 35 U.S.C. § 371 of International Application No. PCT/EP2014/055506, filed Mar. 19, 2014, which claims the benefit of European Patent Application No. 13160384.7, filed Mar. 21, 2013.

BACKGROUND OF THE DESCRIPTION

Field of the Invention

The present invention relates to a method of synthesizing a peptide product comprising at least one hydantoin group. The peptide product may be used as a reference material for the quality control of pharmaceutical peptides, particularly for the quality control of exendin peptides. Further, the invention relates to hydantoin building blocks, a method for manufacturing such building blocks and their use for the synthesis of peptide products.

Description of Related Art

Using well-known recombinant DNA and chemical solid phase synthesis processes, several proteins and peptides have been synthesized for pharmaceutical use. The production of these proteins and peptides, however, often leads to a multiplicity of undesired synthesis by-products. This is especially the case when they are produced by solid phase synthesis. With an increase in length of the peptide/protein, leading to an increase in the synthesis steps, these by-products may be present in 50 to 70% of the crude product.

The synthesis of hydantoin building blocks for the peptide synthesis is known from Zhang et al., J. Org. Chem. 71 (2006), 1750-1753; Opacic et al., J. Pept. Res. 66 (2005), 85-93; Vazquez et al., Chem. Med. Chem. 3 (2008), 979-985; Takeuchi et al., Chem. Commun. (2000), 785-786; Nefzi et al., Bioorg. Med. Chem. Lett. 8 (1998), 2273-2278; Lamothe et al., J. Comb. Chem. 4 (2002), 73-78; Chong and Petillo, Tetrahedron Lett. 40 (1999), 2493-2496, and Park and Kurth, Tetrahedron Lett. 41 (2000), 7409-7413.

The above documents describe the solid phase synthesis of hydantoin compounds. The preparation of hydantoins comprising acid-labile protected side chains, however, is not known.

SUMMARY OF THE DISCLOSURE

The present inventors describe a novel synthesis of hydantoin containing peptide products from dipeptides having side chains protected by acid-labile protecting groups such as trityl (Trt), tert-butyl (tBu) or butoxy-carbonyl (Boc). The resulting hydantoins may comprise trifunctional amino acids with acid labile side chain protecting groups or a combination of a bifunctional amino acid and a trifunctional amino acid with an intact side chain protecting group.

Further, the inventors have provided a novel process for the manufacture of hydantoins on an acid-labile carrier, e.g. a CTC (chlorotritylchloride) resin in combination with a cyclisation e.g. in the presence of a triphosgen.

Furthermore, the application provides novel hydantoin building blocks suitable for the solid phase peptide synthesis in order to prepare peptide products with an N-terminal hydantoin group.

This method is shown exemplarily for the peptide Lixisenatide (AVE0010), a GLP-1 agonist having a length of 44 amino acids long. The amino acid sequence of Lixisenatide is shown in SEQ ID NO:1:

H-G-E-G-T-F-T-S-D-L-S-K-Q-M-E-E-A-V-R-L-F-I-
E-W-L-K-N-G-G-P-S-S-G-A-P-P-S-K-K-K-K-K-K-NH$_2$

Lixisenatide is produced by a chemical solid phase synthesis process.

Figure 1:
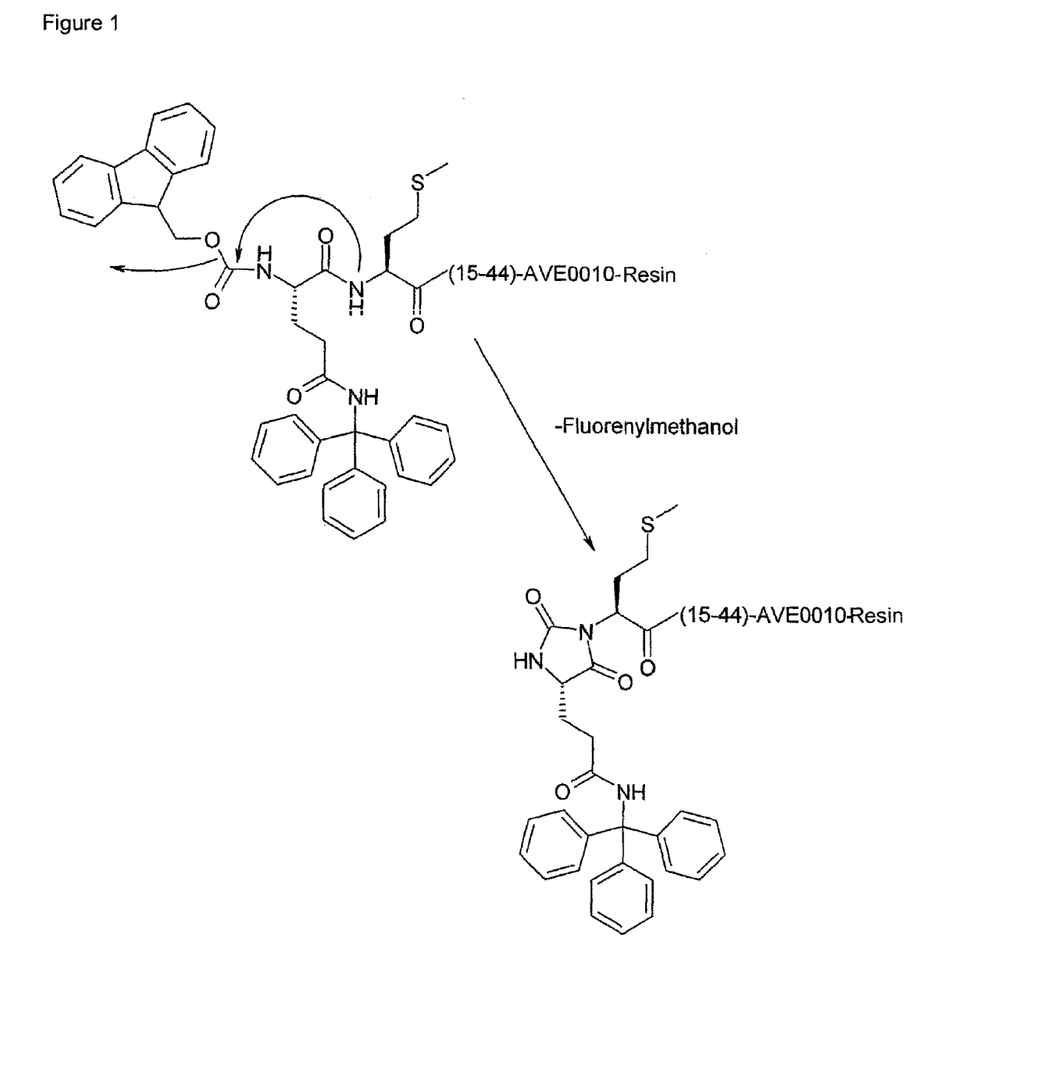
FIG. 1 illustrates the generation of triphenylmethyl-protected. Des[1-12]-hydantoin-(15-44)-AVE0010 by a reaction of the (N-1) amide nitrogen with the carbonyl group of the Fmoc protection group.

In the lixisenatide raw product, several N-terminal hydantoin-containing peptides were found as by-products. It is assumed that they are generated by a reaction of the (N-1) amide nitrogen with the carbonyl group of the Fmoc (Fluorenylmethoxycarbonyl(Fmoc)) protection group as shown in FIG. 1. After removal of fluorenylmethanol, a peptide product comprising an N-terminal hydantoin group is formed leading to a premature termination of the peptide synthesis. The peptide Des [1-12]-hydantoin-(13)-AVE0010 as shown in FIG. 1 was identified as a product which cannot be completely separated from AVE0010 by chromatographic procedures.

Figure 2:
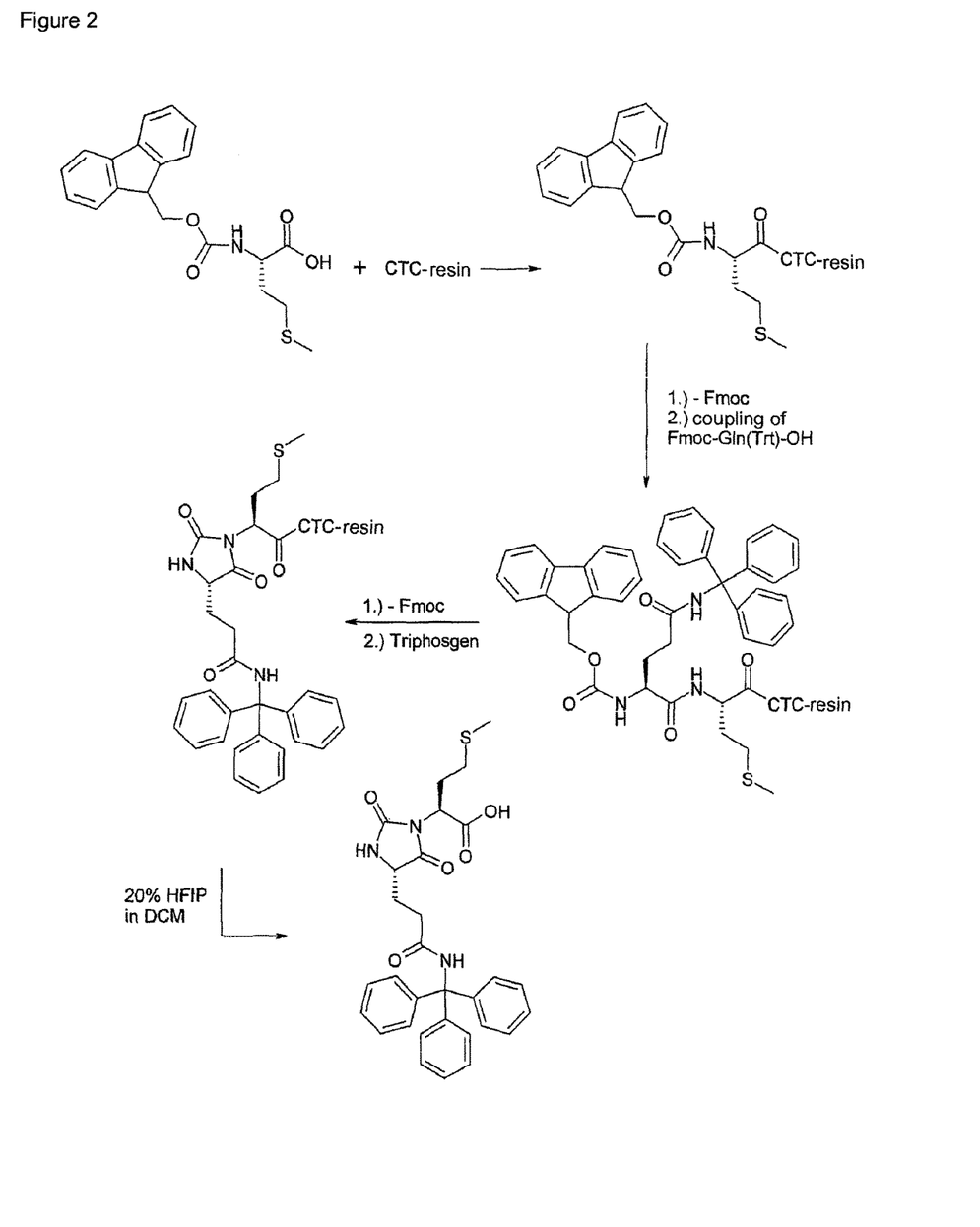
FIG. 2 illustrates the preparation of (S)-2-{(S)-2,5-dioxo-4-[2-(trityl-carbamoyl)-ethyl]-imidazolidine-1-yl}-4-methylsulfanyl butyric acid

The present inventors have now found that a targeted synthesis of peptide products having N-terminal hydantoin groups such as Des[1-12]-hydantoin-(15-44)-AVE0010 (also designated as Des[1-12] modified (13)-AVE0010) is possible by solid-phase peptide synthesis using a specific hydantoin building block. This building block was synthesized by coupling an Fmoc-protected Met building block on a chlorotritylchloride (CTC) resin. After cleavage of Fmoc, a further building block, namely a side chain-trityl (Trt) protected Gln building block was coupled. After further Fmoc cleavage, a cyclization in the presence of triphosgen was carried out. The cleavage of the hydantoin building block from the resin was carried out under mild conditions, e.g. in a 20% solution of hexafluoroisopropanol (HFIP) in dichloromethane (DCM) in order to maintain the acid-labile protecting group on the Gln side chain. The reaction scheme is shown in FIG. 2. The resulting product (S)-2-{(S)-2,5-dioxo-4-[2-(trityl-carbamoyl)-ethyl]-imidazolidine-1-yl}-4-methylsulfanyl butyric acid is a novel compound. This compound can be coupled to a fully-protected peptide product, e.g. H-(15-44)-AVE0010, immobilized on a suitable solid carrier. After treatment with a suitable reagent, e.g. a King's cocktail (King et al., Int. J. Peptide Protein Res. 36 (1990), 255-266), the hydantoin-modified peptide, e.g. Des[1-12] modified (13)-AVE0010 may be cleaved from the carrier.

This principle may be used to prepare any hydantoin building block on a suitable carrier, e.g. CTC resin. Acid labile protecting groups of the original dipeptide are retained. The resulting hydantoin building blocks may be coupled to the N-terminus of peptides in order to provide hydantoin group containing peptides after cleavage from the carrier.

The method of the present invention allows a targeted synthesis of hydantoin group containing peptide products in high yield and purity. These peptide products may e.g. be used as reference materials for the quality control of pharmaceutical peptide products such as lixisenatide.

A subject-matter of the present invention is a method of synthesizing a peptide product comprising an N-terminal hydantoin group of formula (I) or a salt or solvate thereof:

wherein
- $R_1$ and $R_2$ are amino acid side chains,
- P is a peptidic residue, and
- (*) in each case independently denotes an optionally asymmetric C-atom, comprising the steps:

(a) coupling a hydantoin building block of formula (II)

wherein
- $R_{1'}$ is an optionally protected amino acid side chain,
- $R_{2'}$ is an optionally protected amino acid side chain,
- Z is a carboxy group, and
- (*) in each case independently denotes an optionally asymmetric C-atom to a peptide product of formula (III)

wherein
- P' is a peptidic residue optionally comprising protected amino acid side chains, preferably coupled to a solid phase carrier, (b) optionally cleaving off protecting groups from protected amino acid side chains, and
(c) isolating and optionally purifying the peptide product (I).

A further subject-matter of the present invention is a peptide product comprising an N-terminal hydantoin group of formula (I) or a salt or solvate thereof:

wherein
- $R_1$ and $R_2$ are an amino acid side chains,
- P is a peptidic residue, and
- (*) in each case independently denotes an optionally asymmetric C-atom.

Particularly the peptide product is a GLP agonist peptide product, e.g. an exendin peptide product such as exendin-4, liraglutide or lixisenatide (AVE0010) or a GLP-1 receptor agonist like GLP-1(7-36), glucagon, oxyntomodulin and peptides which bind and activate both the glucagon and the GLP-1 receptor (Hjort et al., Journal of Biological Chemistry, 269, 30121-30124, 1994; Day J W et al., Nature Chem. Biol. 5:749-757, 2009) and suppress body weight gain and reduce food intake which are described in patent applications WO 2008/071972, WO 2008/101017, WO 2009/155258, WO 2010/096052, WO 2010/096142, WO 2011/075393, WO 2008/152403, WO 2010/070251, WO 2010/070252, WO 2010/070253, WO 2010/070255, WO 2011/160630, WO 2011/006497, WO 2011/152181, WO 2011/152182, WO 2011/117415, WO 2011/117416, the contents of which are herein incorporated by reference, or GIP and peptides which bind and activate both the GIP and the GLP-1 receptor and optionally the glucagon receptor, and improve glycemic control, suppress body weight gain and reduce food intake as described in patent applications WO 2011/119657, WO 2012/138941, WO 2010/011439, WO 2010/148089, WO 2011/094337, and WO 2012/088116, the contents of which are herein incorporated by reference.

A further subject-matter of the present invention is the use of a peptide product of formula (I) as described above or a salt or solvate thereof as a reference material for the quality control of pharmaceutical peptides, particularly of GLP agonist peptides, e.g. exendin peptides such as lixisenatide.

Still, a further subject-matter of the invention is a reagent kit for determining the amount of impurities in a lixisenatide (AVE0010) product composition comprising:

at least one stock preparation of an N-terminally truncated lixisenatide with an N-terminal hydantoin group, particularly Des [1-12]-hydantoin(15-44)-AVE0010.

Still, a further subject-matter of the present invention is a method for the quality control of a composition comprising a pharmaceutical peptide product, particularly a GLP agonist peptide, e.g. an exendin peptide product, more particularly a lixisenatide (AVE0010) product, comprising quantitatively determining the amount of a peptide product with an N-terminal hydantoin group of formula (I) or a salt or solvate thereof in said composition.

Still a further subject-matter of the present invention is a compound of formula (II) or a salt or solvate thereof:

wherein
- $R_{1'}$ is an optionally protected amino acid side chain,
- $R_{2'}$ is an optionally protected amino acid side chain,
- Z is a carboxy group, and
- (*) in each case independently denotes an optionally asymmetric C-atom.

Still a further subject-matter of the present invention is a method for preparing a compound of formula (II) or a salt or solvate thereof:

wherein
R$_1$, is an optionally protected amino acid side chain,
R$_2$, is an optionally protected amino acid side chain,
Z is a carboxy group, and
(*) in each case independently denotes an optionally asymmetric C-atom,
comprising cyclisizing a carrier bound dipeptide of formula (IV) preferably in the presence of triphosgene:

wherein
R$_1$, R$_2$, and (*) are as described above,
SP is a solid phase carrier, and
X is an amino protecting group,
and cleaving off the cyclisized product from the carrier, preferably under conditions wherein protecting groups at the side chains R$_1$, and/or R$_2$, are retained.

DETAILED DESCRIPTION OF THE DISCLOSURE

The present invention relates to a method of synthesizing a peptide product comprising an N-terminal hydantoin group and a peptidic residue P. The term "peptide product" encompasses peptides and proteins having a length of at least 5 or at least 10 amino acids and up to 50 or up to 100 amino acids or even longer. The peptide product may consist of genetically encoded amino acid building blocks or may comprise non-genetically encoded amino acid building blocks, e.g. non-naturally occurring amino acids, D-amino acids or chemically modified amino acids or may consist of several peptide chains linked e.g. by disulfide bridges. The peptide product may further contain modifications at the N- and/or C-terminus and/or at side chains, e.g. an acylation, an amidation or the addition of non-peptide side chain groups such as lipophilic groups. The peptide product may be linear or circular, wherein circular peptides may be e.g. obtained by coupling of a side chain to the C-terminus. Preferably, the peptide product has a length from 5-100 amino acids.

The peptide product of the invention may be in the form of a salt, e.g. a pharmaceutically acceptable salt or solvate, e.g. a hydrate. Examples of pharmaceutically acceptable salts are described in Remington: The Science and Practice of Pharmacy, (20$^{th}$ ed.) ed. A. R. Gennaro A. R., 2000, Lippencott Williams & Wilkins or in Handbook of Pharmaceutical Salts, Properties, Selection and Use, e.d. P. H. Stahl, C. G. Wermuth, 2002, jointly published by Verlag Helvetica Chimic Acta, Zurich, Switzerland, and Wiley-VCH, Weinheim, Germany. Preferably, the salt is a trifluoroacetate or acetate.

The synthesis of the peptide product is carried out by chemical synthesis procedures, particularly by a solid phase synthesis procedure which is well-known in the art, e.g. a procedure involving a stepwise coupling of synthesis building blocks to a peptide chain bound to a carrier, e.g. a synthetic resin. In a preferred embodiment of the invention, the peptide product is a GLP agonist peptide, particularly an exendin peptide, e.g. exendin-4, liraglutide or lixisenatide (AVE0010), comprising an N-terminal hydantoin group of formula (I). More preferably, the peptide product is an N-terminally truncated peptide product comprising an N-terminal hydantoin group of formula (I) and an amino acid sequence which is N-terminally truncated with respect to the unmodified peptide, particularly a GLP agonist peptide such as an N-terminally truncated exendin peptide, e.g. N-terminally truncated exendin-4, liraglutide, lixisenatide (AVE0010), GLP-1(7-36), glucagon, oxyntomodulin and peptides which bind and activate both the glucagon and the GLP-1 receptor (Hjort et al., Journal of Biological Chemistry, 269, 30121-30124, 1994; Day J W et al., Nature Chem. Biol. 5:749-757, 2009) and suppress body weight gain and reduce food intake which are described in patent applications WO 2008/071972, WO 2008/101017, WO 2009/155258, WO 2010/096052, WO 2010/096142, WO 2011/075393, WO 2008/152403, WO 2010/070251, WO 2010/070252, WO 2010/070253, WO 2010/070255, WO 2011/160630, WO 2011/006497, WO 2011/152181, WO 2011/152182, WO 2011/117415, WO 2011/117416, the contents of which are herein incorporated by reference, or GIP and peptides which bind and activate both the GIP and the GLP-1 receptor and optionally the glucagon receptor, and improve glycemic control, suppress body weight gain and reduce food intake as described in patent applications WO 2011/119657, WO 2012/138941, WO 2010/011439, WO 2010/148089, WO 2011/094337, and WO 2012/088116, the contents of which are herein incorporated by reference. Further examples of peptide products are insulins and insulin analogues or DPP-4 inhibitors, particularly in N-terminally truncated form. Preferably, N-terminally truncated peptide products comprise an N-terminal truncation of at least 2, at least 5 or at least 10 amino acids and retain at least 5, at least 10, at least 15 or at least 20 C-terminal amino acids.

Step (a) of the method of the invention comprises coupling an hydantoin building block of formula (II) to a peptide product of formula (III). The building block is a dipeptidic compound obtainable by cyclisation of a solid phase-coupled dipeptide.

The building block (II) comprises a group Z, wherein Z is a carboxy group capable of coupling to an amino group under coupling conditions, i.e. in the presence of coupling reagents in an organic solvent. Further, the building block (II) comprises two optionally protected amino acid side chains R$_1$, and R$_2$, which may e.g. be selected from His, Asp, Arg, Phe, Ala, Cys, Gln, Glu, Lys, Met, Asn, Ser, Tyr, Thr, Ile, Trp in their D- or L-configuration and unnatural (e.g. non-genetically encoded) amino acids, e.g. as listed in supplier's catalogues and preferably unnatural amino acids with a hetero atom in the side chain such as α-aminoglycine, ornithine, 2,6-diamino-4-hexynoic acid, 4,5-dehydro-lysine, ω-hydroxy-norarginine, co-amino-arginine, β-(2-quinolyl)-alanine, α-methyl-histidine, spinacine, 3-amino-tyrosine, α,γ-diaminobutyric acid, α,β-diaminopropionic acid, β-(1-piperazinyl)-alanine, δ-hydroxy-lysine, homoarginine, ω-methyl-arginine, 4-amino-piperidine-4-carboxylic acid, 2,5-diiodo-histidine, 3-methyl-histidine, 4-amino-phenylalanine, β-(2-pyridyl)-alanine, penicillamine, cis-octahydroindol-2-carboxylic acid, 1,2,3,4-tetrahydroisoquinoline-3-carboxylic acid, β-(3-pyridyl)-alanine, β-fluoro-alanine, β-(2-thienyl)-alanine, β-(3-benzothienyl)alanine, 4-chlorophenyl-alanine, β,β-diphenyl-alanine, β-chloro-alanine, azetidine-2-carboxylic acid, thiaproline, α-methyl-proline, 4-fluoroproline, 4-nitro-phenylalanine, 4-iodo-phenylalanine, 3,4-dichloro-phenylalanine, β-iodo-alanine, 3,4-dehydroproline, 4-bromo-phenylalanine, 3-fluorophenylalanine, 2,6-difluoro-phenylalanine, pipecolic acid, 4-fluorophenylalanine, N—In-methyl-tryptophan, 2,3,4,5,6-pentafluorophenylalanine, β-cyano-alanine, allo-threonine, citrulline, hydroxy-proline, 2-mercapto-histidine, 4-azido-phenylalanine, 3-iodo-tyrosine, α-methyl-trypthophan, 4-methyltrypthophan, 1,2,3,4-tetrahydronorharman-3-carboxylic acid, 4-benzoyl-phenylalanine, ρ-ureido-alanine, pyroglutamic acid, thiocitrulline, β-(2-thiazolyl)-alanine, β-(3,4-dihydroxyphenyl)-serine, 4-cyano-phenylalanine, 3-nitro-tyrosine, 3,5-dibromo-tyrosine, 7-hydroxy-1,2,3,4-tetrahydroisoquinoline-3-carboxylic acid, thyronine, homocysteine, 2-oxothiazolidine-4-carboxylic acid, homocitrulline, β-(1,2,4-triazol-1-yl)-alanine, β-(2-thienyl)-serine, 3-hydroxymethyl-tyrosine, 3,5-dinitro-tyrosine, 3,5-diiodo-tyrosine, 5-hydroxy-trypthophan, β-(7-methoxy-coumarin-4-yl)-alanine, γ-hydroxy-glutamic acid, γ-methylene-glutamic acid, γ-carboxyglutamic acid, α-aminoadipic acid, 2-aminoheptanedioic acid, α-aminosuberic acid, 4-carboxy-phenylalanine, cysteic acid, 4-phosphonophenylalanine, 4-sulfomethyl-phenylalanine, 4-(-7-hydroxy-4-coumarinyl)-aminobutyric acid.

Preferably, $R_{1'}$ and/or $R_{2'}$ are amino acid side chains protected with an acid-labile protecting group such as trityl (Trt), t-butyl (tBu), butoxycarbonyl (Boc), a base-labile protecting group such as fluorenylmethoxycarbonyl (Fmoc), or another protecting group such as carboxybenzyl (Cbz) or allyloxycarbonyl (Alloc) or other protecting groups for hydroxyl-, carboxyl-, amino groups mentioned in Green's Protective Groups in Organic Synthesis, John Wiley & Sons, 4' ed. 2006, chapter 7, Protection for the Amino Group, mentioned in Protecting Groups, P. J. Kocierski, Thieme, $3^{rd}$ ed. 2005, or mentioned in Houben-Weyl, Methods in Organic Chemistry, Synthesis of Peptides and Peptidomimetics, $4^{th}$ ed. 2001. More preferably, $R_{1'}$ and/or $R_{2'}$ are protected Glu, Gln, Asp, Asn, or Ser side chains. In a particularly preferred embodiment, $R_{1'}$ is a protected Glu and/or Gln side chain and $R_{2'}$ is a Met side chain.

Building block (II) further has optionally asymmetric carbon atoms denoted by (*) when $R_1$ and $R_2$ are different from H. Preferably, asymmetric carbon atoms are in the L-configuration.

The peptide product (III) has a free amino group capable of reacting with group Z of hydantoin building block (II) under coupling conditions, i.e. in the presence of coupling reagents in an organic solvent. The peptide product also comprises a peptidic residue P' having preferably at least 5, 10 or 20 amino acids, which is preferably bound to a solid phase carrier, e.g. a resin suitable for peptide synthesis.

The coupling reaction in step (a) is carried out in the presence of a coupling reagent such as TBTU (O-(benzotriazol-1-yl)-N,N,N',N'-tetramethyluronium tetrafluoroborate), HBTU (2-(1H-benzotrialzole-1-yl), 1,1,3,3-tetramethyluronium hexafluorophosphate) or/and HOBT (1-hydroxybenzotriazole)/DIC (diisopropylcarbodiimide) and an organic base such as DIPEA (diisopropylethylamine) in a suitable organic solvent such as DMF (dimethylformamide).

Optional step (b) of the inventive method comprises cleaving off protecting groups from protected amino side chains present in the peptide product. Deprotection is usually carried out at the end of the peptide synthesis in the presence of usual deprotecting agents such as DBU (1,8-diazabicyclo[5.4.0]undec-7-ene), piperidine etc.

Step (c) comprises isolating and optionally purifying the peptide product (I). Step (c) may comprise cleaving the peptide off from the solid phase carrier using suitable cleavage regions such as King's cocktail. These procedures may be carried out under standard conditions as known in the art.

Step (c) may further comprise purifying the peptide product (I) from other peptides obtained in the peptide synthesis procedure. Preferably, the purification involves a chromatographic procedure. The term "chromatographic procedure" involves a chromatographic procedure suitably for the purification of peptide products, including e.g. ion exchange chromatography, hydrophobic interaction chromatography, affinity chromatography, size exclusion chromatography, and particularly high performance liquid chromatography (HPLC) and more particularly Reverse Phase HPLC, or combinations of several procedures. More preferably, the chromatographic procedure involves at least one Reverse Phase HPLC chromatography step.

As a result of the inventive synthesis method, an isolated and purified peptide product comprising a hydantoin group of formula (I) may be obtained. Preferably, this peptide product is substantially free from degradation products, e.g. deamidation products and/or racemised products. Preferably, the amount of degradation products is less than 1%, 0.5% or 0.1% based on the amount of the total product as measured by means of chromatography, e.g. HPLC.

The peptide product is preferably a therapeutic peptide, e.g. an exendin peptide, particularly lixisenatide (AVE0010) having at least one hydantoin group. Preferably, the peptide product is an N-terminally truncated exendin peptide, particularly an N-terminally truncated lixisenatide (AVE0010) having an N-terminal hydantoin group. A specific example of a preferred peptide is which is designated as [Des 1-12]-hydantoin(15-44)-AVE0010 or [Des-1-12]-modified (13)-AVE0010.

The peptide product of the invention may be used as a reference material, e.g. for the quality control of pharmaceutical peptides, particularly for use in a quality control method wherein the amount of undesired hydantoin group containing by-products in a peptide product preparation is quantitatively determined.

Quantitative determination of by-products in a peptide product sample preferably involves mass spectrometry. In addition to mass spectrometry, the determination may involve a prior chromatographic procedure, e.g. in order to separate other impurities from the peptide product or from other ingredients of the composition. Preferably, mass spectrometry is combined with HPLC.

Mass spectrometry is based on a measurement of the mass-to-charge ratio of charged particles. In a typical mass spectrometry procedure, the sample is loaded onto the mass spectrometry instrument and volatilized. The sample components are ionized and the resulting ions are separated in the mass analyzer by electromagnetic fields. The resulting ions are detected and the signal is processed into a mass spectrum. For the ionization of peptide products, electrospray ionization (ESI) and matrix-assisted laser desorption/ionization (MALDI) may be used. The resulting ions may be detected by highly sensitive methods such as Orbitrap or Fourier Transform (FT)-Ion Cyclotron Resonance (ICR) detection systems.

By means of mass spectrometry, a peak derived from a hydantoin group containing by-product may be identified.

Further, the present invention refers to an peptidic hydantoin building block according to formula (II) as described above, the use of this building block for the synthesis of peptides, particularly in the manufacture of a reference material for the quality control of peptide products and to a method for preparing a compound of formula (II).

This method involves cyclisizing a carrier bound dipeptide of formula (IV) as described above in the presence of a cyclization reagent such as triphosgene and optionally a base, e.g. triphosgene/pyridine, triphosgene/triethylamine, triphosgene/imidazole or carbonyldiimidazole optionally in combination with triethylamine or another base. Alternatively, N,N-disuccinimidylcarbonate in presence of 4-dimethylaminopyridine or trimethylsilylchloride in the presence of a base such as triethylamine can be used. The cyclisized product may be cleaved off from the carrier under mild conditions wherein protecting groups, particularly a side labile protecting group at the side chains $R_{1'}$ and/or $R_{2'}$, if present, are retained. Preferably, the solid phase carrier is an acid-labile resin such as a chlorotritylchloride resin, a Wang-resin, a Rink-resin or other acid-labile resins known to the person skilled in the art. The cleaving conditions may involve the use of King's cocktail or other cleavage reagents consisting of varying amounts of TFA or other acidic reagents, thio reagents, water or trisalkylated silanes and mixtures thereof.

Further, the present invention shall be explained in more detail by the following examples describing synthesis, chromatographic purification and analytic characterization of the hydantoin group containing peptide Des[1-12]-hydantoin-(15-44)-AVE 0010.

EXAMPLES

1. Synthesis of Des[1-12]-hydantoin-(15-44)-AVE 0010

Des[1-12]-hydantoin-(15-44) AVE 0010 is a by-product in the synthesis of the pharmaceutical peptide product AVE0010. It is generated when a hydantoin group is formed by cyclization of amino acids Gln (13) and Met (14) and subsequent termination of peptide synthesis (c.f. FIG. 1).

The amino acid sequence of Des [1-12]-hydantoin-(15-44)-AVE 0010 is as follows:

```
                                      (SEQ ID NO: 3)
X-Glu-Glu-Glu-Ala-Val-Arg-Leu-Phe-Ile-Glu-Trp-

Leu-Lys-Asn-Gly-Gly-Pro-Ser-Ser-Gly-Ala-Pro-

Pro-Ser-Lys-Lys-Lys-Lys-Lys-Lys-NH2
```

1.1 Synthesis of the building block 2-{2,5-dioxo-4-[2-(trityl-carbamoyl)ethyl]-imidazolidine-1-yl}-4-methylsulfanyl butyric acid The synthesis started from Fmoc-Met-CTC-resin which was protected by using 25% piperidine in DMF followed by the coupling of Fmoc-Gln(Trt)-OH using HBTU/DIPEA as coupling reagents. The Fmoc group was cleaved again. For ring closure, 23.2 g H-Gln(Trt)-Met-CTC resin were washed with dichloromethane and afterwards treated with 1.5 g triphosgene in neat pyridine. The suspension was agitated overnight. Subsequently, the resin was washed five times with dichloromethane and diisopropylether each and dried under vacuum.

The dried resin was contacted with 100 ml 20% hexafluoroisopropanol in dichloromethane. After stirring for 20 min at room temperature, the liquid phase was removed under nitrogen. The solution was collected and evaporated to dryness after addition of heptane.

The crude product thereby obtained was purified by RP-LC via flash chromatography using a C18-material containing cartridge. For purification, a linear gradient starting from 35% acetonitrile in water plus 0.1% TFA and reaching 80% acetonitrile in water plus 0.1% TFA was used. Fractions were collected and analysed by LC-MS. The product containing fractions were combined and evaporated to dryness after addition of toluene. In total, 1.8 g (S)-2-{(S)-2,5-dioxo-4-[2-(trityl-carbamoyl)-ethyl]-imidazolidin-1-yl}-4-methyl-sulfanyl-butyric acid were obtained.

The identity of the purified product was confirmed by LC-MS: Molecular weight 545.2 g/mol (found), 545.0 g/mol (calculated).

1.2 Synthesis of Des[1-12]-hydantoin-(15-44)-AVE0010

As a starting material, N-terminally Fmoc protected (15-44)-AVE0010 resin was used. The starting material was prepared by solid phase peptide synthesis under standard conditions.

5 g dry Fmoc-(15-44)-AVE0010 resin were mixed with 25 ml DMF, stirred and swollen for 30 min. DMF was then aspirated. After swelling, Fmoc cleavage was carried out in piperidine (25% in DMF).

Then, 709.4 mg (S)-2-{(S)-2,5-dioxo-4-[2-(trityl-carbamoyl)-ethyl]-imidazolidin-1-yl}-4-methyl-sulfanyl-butyric acid (cf. 1.1) were coupled on the starting material in the presence of 503 mg HBTU, 62.8 mg HOBT and 603 µl DIPEA.

The resin was sucked dry and washed with 3×30 ml DMF, 3×30 ml dichloromethane, 3×30 ml methanol and 3×30 ml diisopropylether. After drying overnight, 9.225 g Des(1-12)-hydantoin-(13)-AVE-0010-resin were obtained.

The cleavage of the peptide from the resin was carried out under standard conditions with 2.5 g phenol/2.5 ml $H_2O$/2.5 ml thioanisol/1.25 ml ethandithiol/41 ml trifluoroacetic acid. The yield was 1.49 g Des[1-12]-hydantoin-(15-44)-AVE0010 crude product.

2. Chromatographic Purification of Des[1-12]-hydantoin-(15-44)-AVE0010

Purification was carried out by two RP-HPLC steps and subsequent freeze drying. The RP-HPLC steps were conducted with a Varian PrepStar device. Stainless steel columns packed with C18 reverse phase material (e.g. Daisogel C18) were used as stationary phase. $H_2O$+0.1% trifluoroacetic acid were used as mobile phase A and acetonitrile+0.1% trifluoroacetic acid as mobile phase B. The gradient was carried out at 21-90% mobile phase B.

Figure 3:
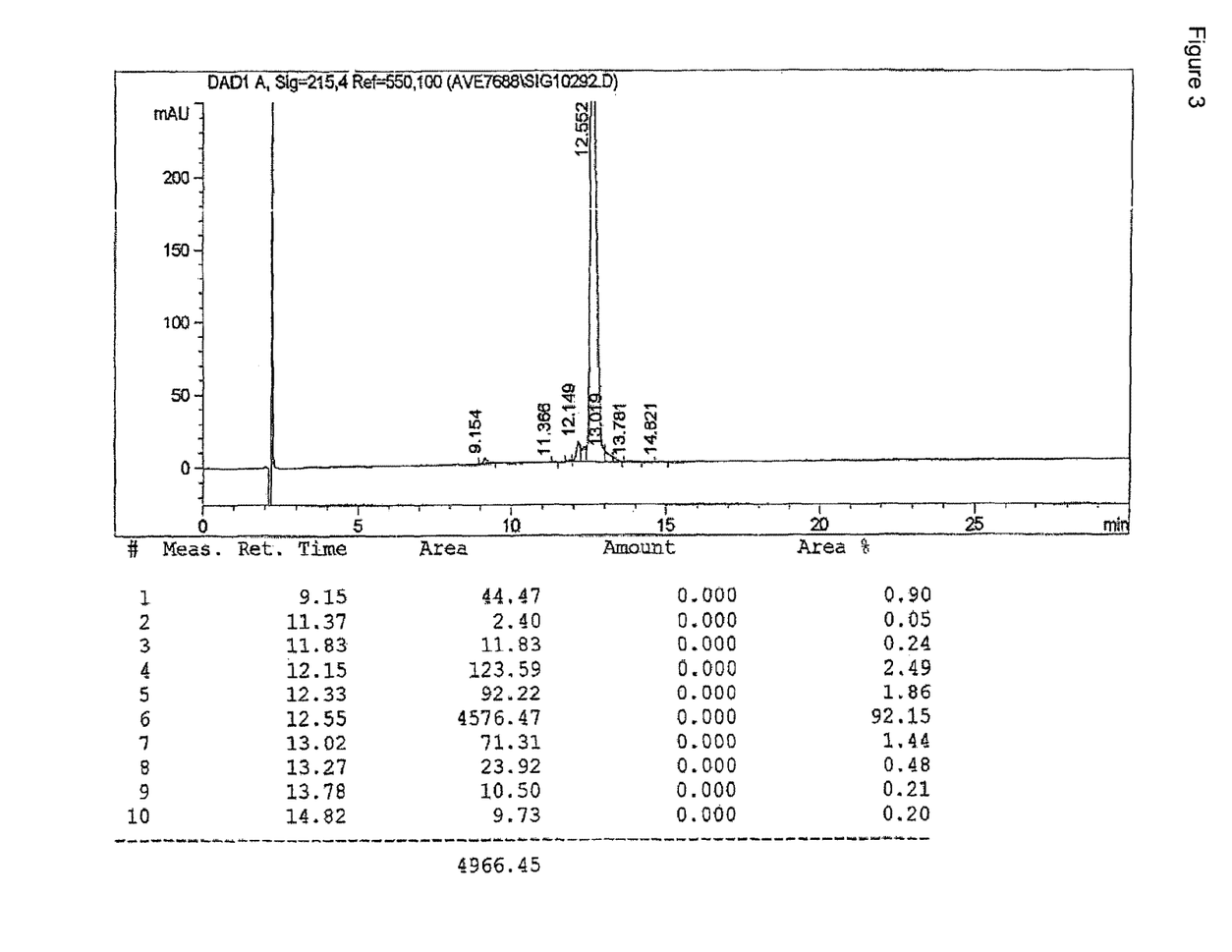
FIG. 3 illustrates the analytical chromatogram of the purified Des[1-12]-hydantoin-(15-44)-AVE0010

0.36 g Des [1-12] hydantoin-(15-44)-AVE0010 with a purity of 92.15% (area % as measured by HPLC) were obtained. An analytical chromatogram of the purified product is shown in FIG. 3.

3. Analytic Characterization

The purified product was characterized mass spectrometrically. Purified AVE0010 was used as a reference standard.

This analytic characterization showed the correct product Des [1-12] hydantoin-(15-44)-AVE0010 with a molecular weight (M+H)+=3623.014. The AVE0010 standard showed a molecular weight of 4856.544. The mass difference of Des[1-12]-hydantoin(13)-AVE0010 to AVE0010 of 1233.53 corresponds to amino acids (His-Gly-Gln-Gly-Thr-Phe-Thr-Ser-Asp-Leu-Ser-Lys-12 $H_2O$+CO). The theoretical monoisotopic molecular weight of Des (1-12) hydantoin-(15-44)-AVE0010 is 3621.95.

The invention claimed is:

1. A method of synthesizing a peptide product comprising an N-terminal hydantoin group of formula:

or a salt or solvate thereof, wherein
P is a peptidic residue Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH$_2$ (SEQ ID NO: 2), and
(*) in each case independently denotes an optionally asymmetric C-atom,
comprising the steps:
(a) coupling a hydantoin building block of formula (II)

wherein
R$_1$' is an optionally protected Gln side chain,
R$_2$' is an optionally protected Met side chain,
Z is a carboxy group, and
each (*) independently denotes an optionally asymmetric C-atom, to a peptide of formula (III)

$$H_2N\text{---}P' \qquad (III)$$

wherein
P' is a peptidic residue P comprising optionally protected amino acid side chains or optional' coupled to a solid phase carrier,
(b) optionally cleaving off protecting groups from protected amino acid side chains, and
(c) isolating and optionally purifying the peptide product.

2. The method of claim 1, wherein R$_1$' and/or R$_2$' are protected with an acid-labile protecting group, a base-labile protecting group, or another protecting group.

3. The method of claim 1, wherein P' is a peptidic residue P coupled to a solid phase carrier.

4. The method of claim 1, wherein the coupling in step s carried out using a coupling reagent and an organic base.

5. The method of claim 4, wherein the coupling reagent is TBTU (O-(benzotriazol-1-yl)-N,N,N',N'-tetramethyluronium tetrafluoroborate), HBTU (2-(1H-benzotrialzole-1-yl)-1,1,3,3-tetramethyluronium hexafluorophosphate); or HOBT (1-hydroxybenzotriazole)/DIC (diisopropylcarbodiimide).

6. The method of claim 4, wherein the organic base is diisopropylethylamine (DIPEA).

7. The method of claim 4, wherein the coupling in step (a) is carried out in dimethylformamide (DMF).

8. The method of claim 1, wherein R$_1$' is a protected Gln side chain.

9. The method of claim 1, wherein R$_2$' is an unprotected Met side chain.

10. A method for the quality control of a composition comprising a pharmaceutical exendin peptide product, comprising quantitatively determining the amount of a peptide product with a hydantoin group according to claim 1, in said composition.

* * * * *

```
                          SEQUENCE LISTING

<160> NUMBER OF SEQ ID NOS: 3

<210> SEQ ID NO 1
<211> LENGTH: 44
<212> TYPE: PRT
<213> ORGANISM: Artificial Sequence
<220> FEATURE:
<223> OTHER INFORMATION: Lixisenatide GLP-1 agonist

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 2
<211> LENGTH: 30
<212> TYPE: PRT
<213> ORGANISM: Artificial Sequence
<220> FEATURE:
<223> OTHER INFORMATION: Synthetic peptide

<400> SEQUENCE: 2

Glu Glu Glu Ala Val Arg Leu Phe Ile Glu Trp Leu Lys Asn Gly Gly
1               5                   10                  15

Pro Ser Ser Gly Ala Pro Pro Ser Lys Lys Lys Lys Lys Lys
            20                  25                  30

<210> SEQ ID NO 3
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: N-terminal hydantoin group
```

```
<400> SEQUENCE: 3

Glu Glu Glu Ala Val Arg Leu Phe Ile Glu Trp Leu Lys Asn Gly Gly
1               5                   10                  15

Pro Ser Ser Gly Ala Pro Pro Ser Lys Lys Lys Lys Lys Lys
            20              25              30
```